(12) United States Patent
Courvoisier et al.

(10) Patent No.: US 11,744,672 B2
(45) Date of Patent: Sep. 5, 2023

(54) DENTAL DRILL

(71) Applicant: STRAUMANN HOLDING AG, Basel (CH)

(72) Inventors: Stéphane Courvoisier, Basel (CH); Eric Jeanbourqin, Basel (CH); Jean-Pierre Pauchard, Basel (CH); Stefan Müller, Basel (CH); Frederik Panse, Basel (CH); Steffen Kühne, Basel (CH)

(73) Assignee: STRAUMANN HOLDING AG, Basel (CH)

( * ) Notice: Subject to any disclaimer, the term of this patent is extended or adjusted under 35 U.S.C. 154(b) by 975 days.

(21) Appl. No.: 16/610,682

(22) PCT Filed: Apr. 30, 2018

(86) PCT No.: PCT/EP2018/061003
§ 371 (c)(1),
(2) Date: Nov. 4, 2019

(87) PCT Pub. No.: WO2018/202605
PCT Pub. Date: Nov. 8, 2018

(65) Prior Publication Data
US 2023/0091999 A1    Mar. 23, 2023

(30) Foreign Application Priority Data
May 2, 2017  (EP) .................................... 17169153

(51) Int. Cl.
*A61C 3/02* (2006.01)
*B23B 51/02* (2006.01)

(52) U.S. Cl.
CPC ................ *A61C 3/02* (2013.01); *B23B 51/02* (2013.01); *A61C 2201/00* (2013.01)

(58) Field of Classification Search
CPC ........ A61C 3/02; A61C 2201/00; B23B 51/02
See application file for complete search history.

(56) References Cited

U.S. PATENT DOCUMENTS

| | | | | |
|---|---|---|---|---|
| 3,633,583 A | * | 1/1972 | Fishbein ............ | A61B 17/1666 606/81 |
| 5,575,650 A | * | 11/1996 | Niznick ............... | A61C 8/0089 433/165 |

(Continued)

OTHER PUBLICATIONS

Jul. 10, 2018 Search Report issued in International Patent Application No. PCT/EP2018/061003.

*Primary Examiner* — Yogesh P Patel
(74) *Attorney, Agent, or Firm* — Oliff PLC

(57) ABSTRACT

The present invention relates to a dental drill (10) formed of titanium or a titanium alloy having a hardness greater than pure titanium, said drill extending along a central axis (A) from a proximal end (14) to a distal end (16). The drill comprises a shank (12) arranged in a proximal end region of the drill (10) and extending along the central axis (A), a flute portion (20) arranged distally to and running coaxially with the shank (12), said flute portion (20) comprising two or more flutes (22a, 22b, 22c) extending along the flute portion (20) and being interposed by lands (24a, 24b, 24c), the flute portion further comprising a central solid web and a drill tip (26) directly adjoining the distal end (28) of the flute portion (20) and comprising two or more flanks (25a, 25b, 25c) which taper radially inwardly from the distal end of each land in the distal direction toward the central axis (A), each flank (25a, 25b, 25c) comprising a cutting edge (30a, 30b, 30c). According to the invention, at the distal end of the drill point (26) at least one groove (32, 33a, 33c) is formed in the web such that the distal most end (36a, 36b, 37b, 37c) of at least one of the flanks (25a, 25b, 25c) is located radially remote from the central axis (A).

21 Claims, 8 Drawing Sheets

(56) References Cited

U.S. PATENT DOCUMENTS

| | | | | |
|---|---|---|---|---|
| 5,967,712 | A | * | 10/1999 | Magill .................. B23D 77/00 |
| | | | | 408/199 |
| 6,547,562 | B2 | | 4/2003 | Kumar |
| 10,456,144 | B2 | * | 10/2019 | Kmiecz .................... A61C 3/02 |
| 10,974,327 | B1 | * | 4/2021 | Bunting ................. B23B 51/02 |
| 2006/0015110 | A1 | * | 1/2006 | Pepper ............... A61B 17/1615 |
| | | | | 606/80 |
| 2006/0127847 | A1 | * | 6/2006 | Danger .................. B23B 51/02 |
| | | | | 433/165 |
| 2006/0263746 | A1 | | 11/2006 | Park et al. |
| 2007/0259307 | A1 | | 11/2007 | Quan et al. |
| 2010/0266357 | A1 | * | 10/2010 | Kretzschmann ........ B23B 51/06 |
| | | | | 408/204 |
| 2014/0294529 | A1 | * | 10/2014 | Takai ..................... B23B 51/02 |
| | | | | 408/229 |
| 2016/0175944 | A1 | * | 6/2016 | Lyu .......................... B23C 5/10 |
| | | | | 407/54 |
| 2017/0274461 | A1 | * | 9/2017 | Mabuchi ................ B23B 51/02 |

* cited by examiner

DENTAL DRILL

The present invention relates to a dental drill formed of titanium or a titanium alloy having a hardness greater than pure titanium.

In oral implantology, dental drills are used for preparing a hole into which a dental implant will ultimately be placed. To this end, the dentist generally uses a series of drills of increasing diameter: in a first drilling step, a pilot hole (or "starter bore") is created using a so-called pilot drill. This pilot hole serves as a guide for one or more larger diameter drills to widen the hole enough to accommodate the dental implant the dentist wishes to place. In traditional drilling workflows, the bore is widened in a series of steps in order to have better control of the final bore geometry and to prevent tissue being affected by excessive drilling that might generate unfavourable heat in the bone tissue.

The majority of dental drills on the market today are manufactured from stainless steel. This material is well-received on the market due to its anti-corrosion and biocompatibility properties.

Notwithstanding the favourable properties of stainless steel drills, other materials are being evaluated which should overcome some shortcomings arising when using stainless steel, or provide unique advantages of their own. In this regard, dental drills made from titanium or a titanium alloy, such as TAV (Ti6Al4V), are of particular interest, since they would provide certain improvements over traditional stainless steel drills. In particular, the use of titanium or a titanium alloy would allow for a greater corrosion resistance and a better biocompatibility of the drill than when using stainless steel. Further, the use of titanium or a titanium alloy would open the possibility to colour the drills by anodization, which enables different drills to be quickly and easily identified by the user. In addition, titanium or titanium alloys can more easily be laser marked. Thus, creating a dental drill formed of titanium or a titanium alloy would be beneficial.

US 2006/0263746 discloses a dental drill formed of titanium such that the drill, and hence any chips generated during use of the drill, are formed of the same material as the dental implant which will later be placed in the bore. The drill is further anodised in order to provide a visual reference to check for abrasion of the drill. U.S. Pat. No. 6,547,562 and US 2007/0259307 both disclose dental instruments which can be formed from a number of different materials including titanium alloys, in particular TAV (Ti-6Al-4V).

Although the use of titanium and titanium alloys to manufacture dental drills provides for the mentioned advantages over stainless steel, it does also present new challenges. This relates in particular to providing the necessary cutting action, which enables the drill to cut through bone in an efficient and controlled manner.

The cutting edges of stainless steel drills are often created by grinding. This procedure results in a very sharp edge and thus a superior cutting function. In order to be ground, the stainless steel must first be hardened. Ultimately, this results in a three-step manufacturing process comprising a machining, a hardening and a grinding step.

Titanium and titanium alloys are softer than hardened stainless steel; hence, it is not possible to grind a workpiece made of these metals. Furthermore, it is not possible to harden titanium or titanium alloys. Therefore, alternative ways must be found to provide a titanium or titanium alloy drill with a suitable cutting ability to drill into bone.

The object of the present invention is therefore to provide a dental drill, which is made of titanium or a titanium alloy, but which nevertheless provides for adequate cutting ability to drill into bone.

According to one aspect the present invention provides a dental drill formed of titanium or a titanium alloy having a hardness greater than pure titanium, said drill extending along a central axis from a proximal end to a distal end, the drill comprising a shank arranged in a proximal end region of the drill and extending along the central axis, a flute portion arranged distally to and running coaxially with the shank, said flute portion comprising two or more flutes extending along the flute portion and being interposed by lands, the flute portion further comprising a central solid web, and a drill point directly adjoining the distal end of the flute portion and comprising two or more flanks which taper radially inwardly from the distal end of each land in the distal direction toward the central axis, each flank comprising a cutting edge, wherein at the distal end of the drill point at least one groove is formed in the web such that the distal most end of at least one of the flanks is located radially remote from the central axis.

Accordingly the present invention relates to a dental drill extending along a central axis from a proximal end to a distal end. Regarding its dimensions, the length and diameter of the drill are limited to a size allowing it to be used in the oral cavity of a human patient. Specifically, the dental drill of the present invention is adapted to drill bone in order to prepare a hole in a patient's jawbone into which a dental implant is to be placed. In this regard, both pilot drills for preparing a pilot hole or a starter bore in the bone as well as drills for widening the pilot hole are encompassed by the present invention.

According to the present invention, the dental drill is made of titanium, or a titanium alloy having a greater hardness than pure titanium. Thus, throughout the specification, all references to a "titanium alloy" in the context of the present invention should be interpreted as a titanium alloy having a greater hardness than pure titanium.

As further defined in claim 1, the dental drill comprises a shank arranged in a proximal end region of the drill and extending along the central axis. The shank is designed to cooperate with a drive tool, such as a dental handpiece, and generally has an anti-rotational portion, e.g. with a polygonal cross-section, tang, tenon or standard dental coupling, adapted to receive torque from a drive tool.

The dental drill of the present invention further comprises a flute portion arranged distally to and running coaxially with the shank. The flute portion comprises two or more flutes extending along the flute portion and being interposed by lands. In other words, the lands are defined by the outer surface formed between two neighbouring flutes. The flute portion can be cylindrical or tapered along all or part of its length. For example, it is common for drills to comprise a back taper along the flute portion. In addition the web, namely the solid core located between the base of the flutes, can have a constant diameter along the length of the flute portion or it may be tapered along all or part of its length. The outer diameter of the flute portion and the diameter of the web can be altered independently of each other. For example, by altering the depth of the flutes along the length of the flute portion it is possible for the overall diameter of the flute portion to remain constant while the web tapers in a distal direction, or alternatively to create a tapered outer diameter while the diameter of the web remains constant.

Directly adjoining the distal end of the flute portion, a drill point is formed comprising two or more flanks which taper radially inwardly from the distal end of each land in the distal direction toward the central axis. Each flank comprises a cutting edge, and thus the drill point comprises two or more cutting edges. Specifically, the two or more cutting edges run inwardly from an outer circumference of the drill point, which is equal to the distal end of the flute portion.

The dental drill of the present invention has the characterizing feature that, at the distal end of the drill point, at least one groove is formed in the web such that the distal most end of at least one of the flanks is located radially remote from the central axis.

This has the effect of preventing, or at least limiting, the so-called "dead metal" of the drill. This metal does not provide a cutting function, creates friction and requires force to rotate this against and into the bone. Removing at least a part of this dead metal increases the efficiency and cutting ability of the drill.

The provision of a groove, or grooves, in accordance with the present invention effectively "cuts off" at least one flank, and hence its cutting edge, before it reaches the central axis and means that the distal most end of the flank is located radially remote from the central axis. It should be noted that, although the at least one groove of the present invention is formed in the web of the drill point, the groove is not limited to the web and, depending on drill design, may additionally extend radially beyond the web into the wall (face) of the flute. Further, in addition to these "cut off" grooves, other grooves can also be present on the drill point, as will be discussed further below.

The provision of at least one groove at the distal end of the drill point in accordance with the present invention is preferably achieved according to one of the following concepts:

In the first concept, the at least one groove is provided such that the distal most end of all of the flanks are located radially remote from the central axis. In this way, no material is present at the central axis at the distal end of the drill point and hence a pillar of bone material is continuously formed in the centre of the drilling hole, said pillar being destroyed (owing to the porous nature of the bone material) as the drill moves deeper into the bone. Thus, an increase in the drilling rate can be achieved without exerting higher loads.

The geometry of the first concept can be achieved by providing a separate groove for each flank, such that an equal number of grooves and flanks is provided, one groove being located across the radially innermost portion of each flank such that the distal most end of each flank is radially remote from the central axis. These grooves can additionally provide a web thinning function, in order to extend the length of, or change the shape of, the cutting edges, as will be explained in more detail below in relation to the second concept. Alternatively, the drill point can comprise separate web thinning or other grooves in addition to the "cut off" grooves of the present invention.

Preferably the drill has between two and four flutes, and hence also the same number of lands and flanks. In one preferred embodiment the drill comprises at least three, preferably exactly three, flutes, lands and flanks, and at least three, preferably exactly three, grooves in the web of the drill point, each groove being located across the radially innermost portion of a flank such that the distal most end of each flank is radially remote from the central axis.

In another preferred embodiment of the first concept, the drill comprises two flutes, lands and flanks. In such embodiments, the symmetrical nature of the drill point means that a single central groove can be located across the radially innermost part of both flanks such that the distal most end of each flank is radially remote from the central axis.

Therefore, in one particularly preferred embodiment of the first concept, the flute portion comprises exactly two flutes interposed by exactly two lands and the drill point comprises exactly two flanks. A central groove is formed at the distal end of the drill point, said groove running through the central axis across the web of the drill, i.e. across the central portion of the drill body between the bases of the flutes, such that the distal most ends of both flanks are located radially remote from the central axis. In this way, no material is present at the central axis at the distal most end of the drill.

This design is beneficial for drills having just two flanks, as the symmetrical nature of the drill point means such a groove can be easily machined into the drill point in a manner which maintains the 2-fold symmetry of the drill point.

The introduction of such a groove into titanium or titanium alloy drills has been found to significantly increase the cutting ability of the drills, to the extent that certain drills unable to cut through bone prior to the introduction of the aforementioned groove become capable of providing the necessary cutting function to enable a pilot or starter bore to be created.

Drills having only two flutes, and hence also only two lands and only two flanks, are particularly used within the dental field at small diameters, as at such small diameters a greater number of flutes would not have the necessary volume to transport bone chips away from the cutting edges. Therefore, drills according to this preferred embodiment of the first concept preferably have a cutting diameter of 2.5 mm or less, most preferably between 2 mm and 2.4 mm. However, it is also possible to use this drill geometry in dental drills of larger diameter, e.g. up to 7 mm. By "cutting diameter" it is meant the maximum cutting diameter of the drill, which is usually defined by the largest diameter of the cutting edges of the flanks or, where present, the cutting edges of the lands.

Preferably the central groove width is in the range of 0.05 to 0.5 mm, preferably of 0.15 to 0.3 mm. Thus, the distance between the distal most ends of the two flanks arranged on opposite sides of the groove is in the same range, i.e. is from 0.05 to 0.5 mm, preferably from 0.15 to 0.3 mm. Preferably the depth of the central groove (measured from the bottom of the groove up to the height of the distal most ends of the flanks) is approximately or exactly equal to the groove width. Therefore, preferably the depth of the central groove is from 0.05 to 0.5 mm, more preferably from 0.15 to 0.3 mm.

The central groove extends across the web of the drill from flute base to flute base (i.e. the radially innermost part of each flute) such that, in this embodiment, the groove is only present in the web of the drill point. The length of the groove is thus dependent on the diameter of the web at the distal end of the drill point. Typically the diameter of the web, and hence the groove, is within the range of 10% to 20% of the cutting diameter. Thus, in embodiments in which the cutting diameter is between 2 mm and 2.4 mm the groove length is preferably from 0.2 to 0.48 mm. In a particularly preferred embodiment the groove length is approximately 0.3 mm.

With further regard to this preferred two-flute embodiment of the first concept, it is preferred that the cutting edges of the flanks are curved. This shape is easier to manufacture as the cutting edges can simply follow the curve of the flutes. In other words, the cutting edges can be formed by the intersection of the leading edge of the flank with the flute over the entire radial length of the cutting edge. This means that the cutting edges run inwardly from the outer diameter of the drill point but do not converge on the central axis. This design of cutting edge is particularly beneficial in drills having a cutting diameter of 2.5 mm or less, as at such small diameters a simple drill point geometry is easier to produce. In other embodiments however the cutting edges may be straight or angled and/or may converge on the central axis, e.g. by means of web thinning grooves.

With further regard to this preferred two-flute embodiment of the first concept, it is additionally or alternatively preferred that each flank comprises a trailing surface having a greater angle than the relief angle, i.e. the angle between the flank surface formed directly behind the cutting edge and a plane perpendicular to the drill axis. This trailing surface can increase the bite of the drill without making this too aggressive.

According to the second concept of the present invention, the distal most end of at least one flank is located at the central axis and the at least one groove is formed in the web such that the distal most end of at least one flank is located radially remote from the central axis.

In other words, in this second concept, one or more flank is not "cut off" by a groove and hence continues to taper distally to the central axis. This enables at least one cutting edge to extend closer to the central axis than the cutting edges of flanks which have been cut off by a groove. In this way, a cutting function is provided closer to the central axis while still reducing the material present at the distal end of the drill point.

Preferably, the cutting edge of the at least one flank whose distal most end is located at the central axis is positioned on the flank such that the cutting edge extends to the central axis. In this way, the drill provides a cutting function across the full radial length of the drill point.

Preferably, in relation to the second concept, the at least one groove of the present invention is positioned such that it cuts across the radially innermost part of a flank. When a plurality of grooves according to the present invention is provided, each groove is preferably positioned such that it cuts across the radially innermost part of a separate flank. In this way, each separate groove effectively "cuts off" one flank. It should be noted that, as mentioned above, although each groove is formed in the web of the drill point, the groove is not limited to the web and, depending on drill design, may additionally extend radially beyond the web into the wall (face) of the flute. Further, in addition to these "cut off" grooves, other grooves can also be present on the drill point, as will be discussed further below.

Preferably, in order to limit the material at the distal end of the drill point, the distal most end of a single flank is located at the central axis and at least one groove is formed in the web such that the distal most end of the one or more remaining flank is located radially remote from the central axis. Thus, in this preferred embodiment, only the distal most end of a single flank is located at the central axis while all other flanks of the drill point are cut off by the one or more groove of the present invention.

As mentioned above, in relation to the second concept, the cutting edge of at least one flank preferably extends to the central axis. In such embodiments therefore, the cutting edge cannot be formed solely by the intersection of the leading edge of the flank and the flute.

In order to extend the cutting edge of one or more flank radially inwards into the web of the drill, preferably, in relation to the second concept, to the central axis, web thinning grooves can be provided in the drill point. Such grooves can be used on curved, straight or angled cutting edges. Such web thinning grooves can be provided in addition to the "cut off" grooves of the present invention. However, in particularly preferred embodiments, the at least one groove of the present invention is arranged to extend the cutting edge of one flank radially inwards into the web while also cutting across the radially innermost part of a neighbouring flank such that the distal most end of the neighbouring flank is radially remote from the central axis. In this way the "cut off" groove or grooves of the present invention can provide a dual function; namely removing material from the central axis at the distal end of the drill while also extending the cutting edge of a flank into the web of the drill.

If such "dual function" grooves are provided in respect of each flank of the drill point, then the distal most ends of all the flanks will be radially remote from the central axis, and hence such an embodiment would fall under the first concept. In relation to the second concept, in which the distal most end of at least one flank is located at the central axis, if it is desired to extend all of the cutting edges into the web of the drill point, then at least one web thinning groove must be provided which stops short of the radially innermost part of a neighbouring flank, and hence only provides a web thinning function. Therefore, in relation to the second concept, the drill point preferably further comprises at least one additional web thinning groove which is arranged to extend the cutting edge of one flank radially inwards into the web but which does not cut across the radially innermost part of a neighbouring flank, such that the distal most end of this flank is located at the central axis.

As will be appreciated, the creation of such web thinning grooves and dual function grooves is more complicated at smaller diameters. Therefore, the preferred geometry of the second concept is most suited for dental drills having a relatively large cutting diameter, e.g. 2.5 mm or greater.

At larger diameters of drill more than two lands are preferred in order to increase stability and prevent rattling of the drill. Further, as mentioned above, at larger diameters it becomes possible to use a larger number of flutes while maintaining a suitably large flute volume in order to effectively transport bone chips away from the cutting edges. Thus, in general it is preferred that drills comprising three or more flutes have a cutting diameter of at least 2.5 mm, more preferably a cutting diameter of between 2.5 mm and 7 mm.

As at least preferred embodiments of the second concept are easier to manufacture in relatively large diameter drills, and as such drills can have three or more flutes, the second concept of the present invention is particularly preferred for drills having at least three flutes, and hence also at least three lands and at least three flanks.

In a preferred embodiment therefore, in relation to the second concept, the flute portion comprises at least three flutes, interposed by at least three lands. The drill point therefore comprises at least three flanks, the distal most end of at least one of said flanks being located at the central axis and one or more grooves being formed in the web such that the distal most end of at least one flank is located radially remote from the central axis.

In a particularly preferred embodiment, in relation to the second concept, the flute portion comprises exactly three flutes and, hence, exactly three lands and the drill point comprises exactly three flanks. Preferably, the distal most end of one of the flanks is located at the central axis and a plurality of grooves are formed in the web such that the distal most end of the two remaining flanks are located radially remote from the central axis.

In one particularly preferred embodiment, in which the drill point comprises exactly three flanks, the drill point further comprises three grooves in the web of the drill point, each groove arranged to extend the cutting edge of a separate flank radially inwards into the web, wherein two of said grooves further cut across the radially innermost part of a neighbouring flank such that the distal most end of two of the flanks are located radially remote from the central axis, the third groove stopping short of the radially innermost part of a neighbouring flank such that the distal most end of this flank is located at the central axis. In this embodiment the cutting edges are preferably straight and each extends along a radial line, such that the cutting edge of one flank extends to the central axis.

More generally, in relation to the second concept, it is preferred that the cutting edges of the two or more flanks are straight and extend along a radial line, such that the cutting edge of one flank extends to the central axis.

Larger diameter dental drills, e.g. with a cutting diameter of 2.5 mm or greater, are often intended to widen a pre-existing pilot or other bore hole. It is typically recommended that such later stage drilling takes place at a low feed rate, in order to prevent excessive heat generation and/or placement errors.

For the titanium or titanium alloy drills according to the present invention, it has been found that a steeper relief angle than is typically used in standard stainless steel drills is preferred, particularly in relation to drills recommended to be driven at low feed rates. Preferably therefore, particularly in relation to drills having a cutting diameter of at least 2.5 mm and/or having three or more flutes, each flank has a relief angle of at least 18°, preferably 18° to 30°, more preferably 21° to 28°, most preferably 24° to 26°. As known to the skilled person and as will be illustrated below, the "relief angle" refers to the angle between the flank surface formed directly behind the cutting edge and a plane perpendicular to the drill axis.

With the relief angle lying in the range mentioned above, this embodiment of the present invention is in quite clear contrast to traditional stainless steel drills, which typically have smaller relief angles, in order to prevent an overly aggressive drill action. Such high relief angles are therefore not desirable in stainless steel drills. In titanium or titanium alloy drills however, these higher relief angles compensate for the softer nature of the drill material and enable this to "bite" into the bone. By the upper limit of the preferred relief angle range, it is avoided that the drill runs too deep too quickly. By the lower limit, it is avoided that the drill is unable to cut into the bone. Ultimately, a well-balanced drilling performance of a fast cutting action but nevertheless a good controllability of the drill can be achieved.

Alternatively or additionally, the cutting edges of the flanks of drills having a cutting diameter of at least 2.5 mm and/or at least three flutes are preferably straight, as this makes the drill more controllable and less aggressive. Preferably the straight cutting edges run inwardly along a radial line from the outer diameter of the drill point towards the central axis.

As the drill design of the second concept is particularly preferred for drills having at least three flutes, the above preferred features relating to drills having three or more flutes are preferably used in combination with the drill geometry of the second concept.

According to the present invention, the dental drill is made of titanium or a titanium alloy having a greater hardness than pure titanium. A titanium drill can be beneficial as this allows the drill to be made of the same material as the dental implant and has the highest biocompatibility. However, preferably the drill is formed of a titanium alloy having a greater hardness than pure titanium and hence provides a better cutting function. A dental drill made of a titanium-aluminium alloy, in particular a titanium-aluminium-niobium alloy, such as TAN, or a titanium-aluminium-vanadium alloy, such as TAV, is particularly preferred due to the materials' strength and hardness. In a particularly preferred embodiment the dental drill is made of TAN, which exhibits a particularly beneficial biocompatibility in relation to TAV. This is due to the possibility of corrosion of drill chips within the mouth. Should any such corrosion happen niobium has a greater biocompatibility than vanadium.

According to a preferred embodiment of the present invention, in respect of either the first or second concept, at least one of the cutting edges is interrupted by at least one groove to form a discontinuous cutting edge. In other words, the interrupting groove divides the cutting edge of one and the same flank into two different portions, which extend on either side of the groove. For this reason the interrupting groove of this preferred embodiment is different to the one or more "cut off" groove described above, which is located at the radially innermost part of the flank and acts to terminate the cutting edge. Surprisingly it has been found that a drill according to this embodiment is particularly good at enabling the titanium or titanium alloy drill to directly drill into bone, i.e., in situations in which a pilot drill has not been used to create a pilot hole.

Preferably each of the flank cutting edges comprises at least one interrupting groove. Although numerous grooves can be included in each cutting edge, in view of the relatively small size of dental drills, it is preferred that one or more of the cutting edges, preferably each cutting edge, is interrupted by a single groove.

Although the interrupting groove or grooves formed in each cutting edge could be located at the same radial location, it is preferred that the at least one, preferably single, interrupting groove is located at a different radial location in each cutting edge. In this way the grooves are "staggered" relative to each other and thus ensure a more even cutting function over the surface area of the drill point.

The interrupting groove(s) preferably run approximately or exactly perpendicular to the cutting edge which they interrupt and extend at least partially across the flank surface. In particularly preferred embodiments at least one interrupting groove does not extend over the entire surface of the flank.

The width of the interrupting groove, along the cutting edge, is preferably between 0.25-1 mm, most preferably 0.5 mm. This creates the desired interruption to the cutting edge while still maintaining a relatively long cutting edge.

Preferably the one or more interrupting groove is used in drills having a cutting diameter of 2.5 mm or greater.

This is because it is easier to form such interrupting grooves on these relatively larger drills. The interrupting grooves can be used with drills having the geometry of either of the above concepts. However, as discussed above, the drill geometry of the second concept is often used in drills having a larger diameter. Thus, preferably, the at least one interrupting groove is used in combination with the second concept. Thus, in one particularly preferred embodiment, the drill comprises three flutes, lands and flanks, the distal most end of one of said flanks being located at the central axis while grooves are formed in the web such that the distal most end of the other two flanks are located radially remote from the central axis, the cutting edge of each flank being interrupted by a single groove to form a discontinuous cutting edge. In this preferred embodiment the interrupting grooves of each cutting edge can be staggered as discussed above. Alternatively, or in addition, in this embodiment the cutting diameter of the drill is preferably at least 2.5 mm. Alternatively, or in addition, the cutting edges of the flanks are straight and extend along a radial line, the cutting edge of one of said flanks extending to the central axis.

The above discussed one or more interrupting groove can also be used in combination with the drill geometry of the first concept at both large and small cutting diameters, e.g. 2 mm to 7 mm.

According to the present invention, the flute portion of the drill comprises two or more flutes. While these flutes, and hence the interposed lands, can extend linearly along the flute portion, parallel to the central axis, it is preferred that both the flutes and the lands run helically along the flute portion. This assists in bone chip removal from the drill point.

According to the present invention, the flanks of the drill point each comprise a cutting edge. In addition, the lands of the drill may also each comprise a cutting edge. In such embodiments, the cutting edge of each land extends at least along a length of the flute portion such that the drill can provide a side cutting action. This is particularly beneficial for drills, such as the pilot drill, which are intended to be used for direct drilling in the bone, i.e. without a pre-existing bore hole and which may need to correct the angle of the bore hole.

In preferred embodiments the cutting edge of each land extends the length of the flute portion. This is particularly preferred in drills having a smaller cutting diameter, i.e. under 2.5 mm. In other embodiments however the cutting edge of each land only extends within the first half, preferably the first quarter, of the flute portion, as measured from the distal end. In still further embodiments the cutting edge of each land can be blunted at least along a portion of the flute portion in order to control the cutting performance in the radial direction. This is particularly preferred in drills having a larger cutting diameter, i.e. over 2.5 mm.

The cutting edge of each land is formed at the intersection of the flute with the leading edge of the land. In the same manner, the cutting edge of each flank is formed, at least in the radially outer region of the drill point, by the intersection of the leading edge of the flank with the flute. In some embodiments, as discussed above, web thinning grooves can be provided in the drill point in order to extend the cutting edge radially inwards and/or to alter the shape of the cutting edge. In such cases at least part of the cutting edge is therefore formed at the intersection of the leading edge of the flank with said web thinning groove. As mentioned above, the cutting edges of the flanks can be curved or these may be straight or angled. In relation to the second concept, the cutting edges of the drill point are preferably straight and extend along a radial line, whereas in relation to the first concept the cutting edges are preferably curved.

With further regard to either the first or second concept, it can be preferred that the flute portion comprises one or more stepped portion. This can be beneficial particularly when the drill is intended for use in placing a tapered implant. In order to create a suitably shaped bore hole, it is preferable that the drill mimics the shape of the implant which will be introduced into the bore. However, when an implant is apically tapered, a correspondingly shaped drill, i.e. with a distally tapering flute portion, could create an overly aggressive cutting action, making the drill harder to control. Providing one or more stepped portion in the flute portion allows the drill to mimic an apically tapering implant without the cutting action being too aggressive.

Preferably the flute portion comprises between one and three stepped portions, preferably two stepped portions. Preferably the one or more stepped portion is located towards the distal end of the flute portion, in the vicinity of the drill point, although these can also be located more proximally, depending on the shape of the implant to be mimicked. Each stepped portion is formed by a step-wise reduction in diameter towards the distal end of the flute portion. The step formed at the change in diameter can extend perpendicular to the central axis or preferably tapers radially inwards in the distal direction. The intersection of the leading edge of the lands and the flutes over the step form a cutting edge, in order to enable the step to widen the bore hole and thus better mimic the shape of the implant. For the avoidance of doubt, when a flute portion comprises one or more stepped portion, the "cutting diameter" of the drill refers to the maximum cutting diameter of the flute portion.

As mentioned above, the diameter of the drill is limited to a size allowing it to be used in the oral cavity of a patient. The cutting diameter of the drill is preferably no greater than 7 mm. Given the fact that the drill is primarily designed for drilling bone to prepare a hole into which a dental implant is to be placed, it is further preferred that the cutting diameter is at least 2 mm. Thus, a typical cutting diameter of the dental drill ranges up to about 7 mm and specifically include diameters of 2.2 mm (for a pilot drill), 2.8 mm, 3.5 mm, 4.2 mm, 4.8 mm and 6.2 mm (for the drills used subsequently).

The length of the drill is preferably from 25 to 45 mm, and the length of the flute portion is preferably from 10 to 26 mm.

According to a further embodiment relating to both the first and the second concept, the drill is preferably matted, preferably via acid etching. Thus, a matte finish is created and, hence, the reflection of light is reduced. As a result, it is easier for the surgeon to see any depth marking present on the drill during surgery. Such depth markings are preferably formed by laser marking. Preferably, the drills are acid etched using an etching solution containing a mineral acid, preferably $HNO_3$, in particular for a duration of less than 1 minute at room temperature. Thus, the desired matte finish can be achieved on the dental drill of the present invention in a very simple and straightforward manner. In particular, the etching is even simpler and shorter than when using stainless steel as the material of the drill, since a corresponding matting of stainless steel requires etching for more than 5 minutes over multiple treatments.

As mentioned above and in contrast to a drill made of stainless steel, the use of titanium or a titanium alloy allows the drill of the present invention to be easily anodized. Thus, drills having different colours can be created such that the surgeon can quickly and easily identify drills of a particular diameter etc. Preferably therefore, the drill of the present invention is anodized.

Preferably the dental drill of the present invention is integrally formed in one monolithic piece. This eases manufacture.

Preferred embodiments of the present invention will now be described, by way of example only, with reference to the attached figures, in which.

Figure 1:
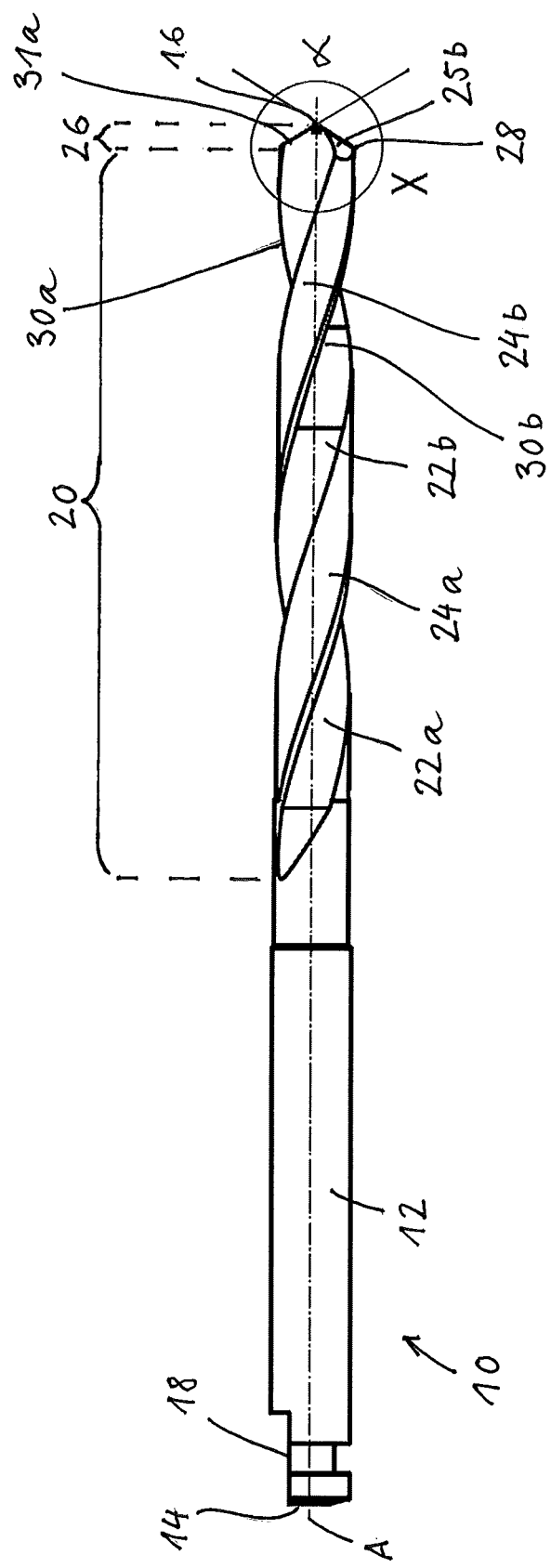
FIG. 1 shows a side view of a first embodiment of a dental drill according to a preferred embodiment of the first concept of the present invention from a direction of view perpendicular to the central axis.
Figure 2:
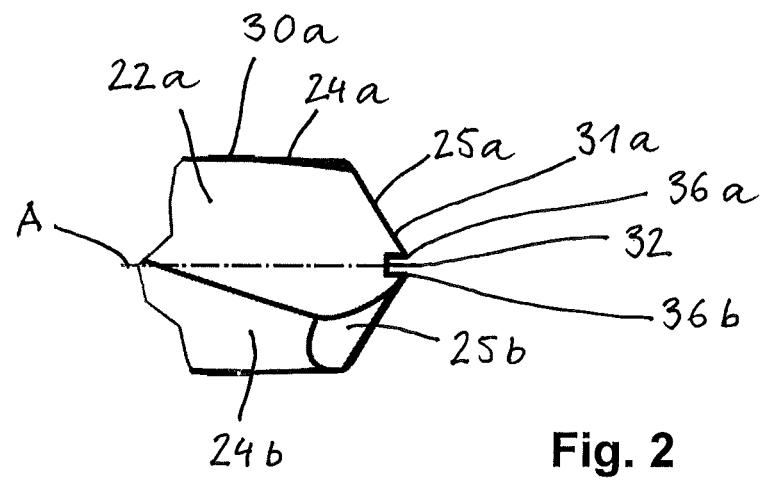
FIG. 2 shows a magnified view of the distal end region of the embodiment shown in FIG. 1 marked as detail X in FIG. 1.
Figure 3:
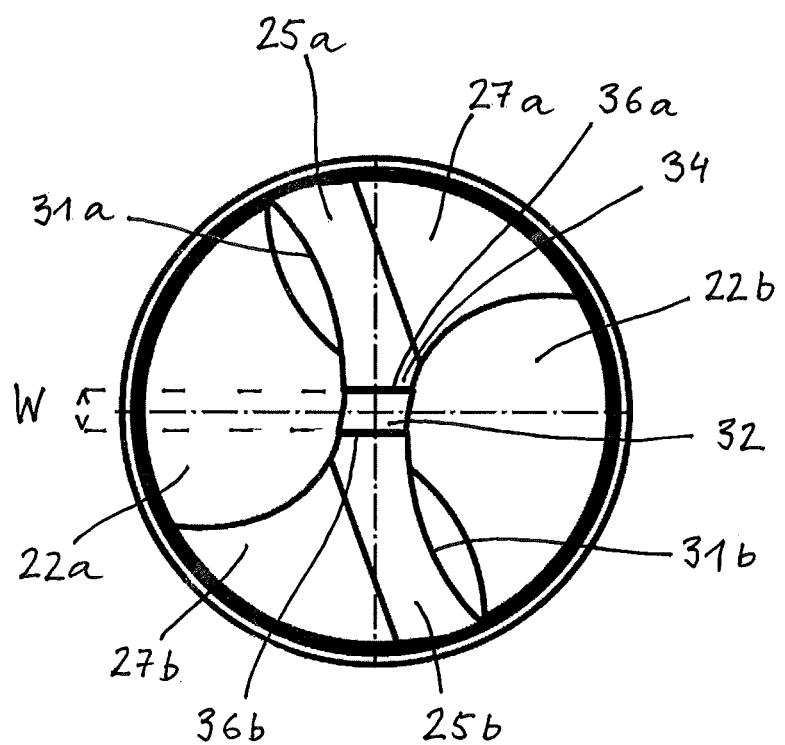
FIG. 3 shows a front view of the drill tip of the embodiment shown in FIG. 1 from a direction of view along the central axis.
Figure 4:
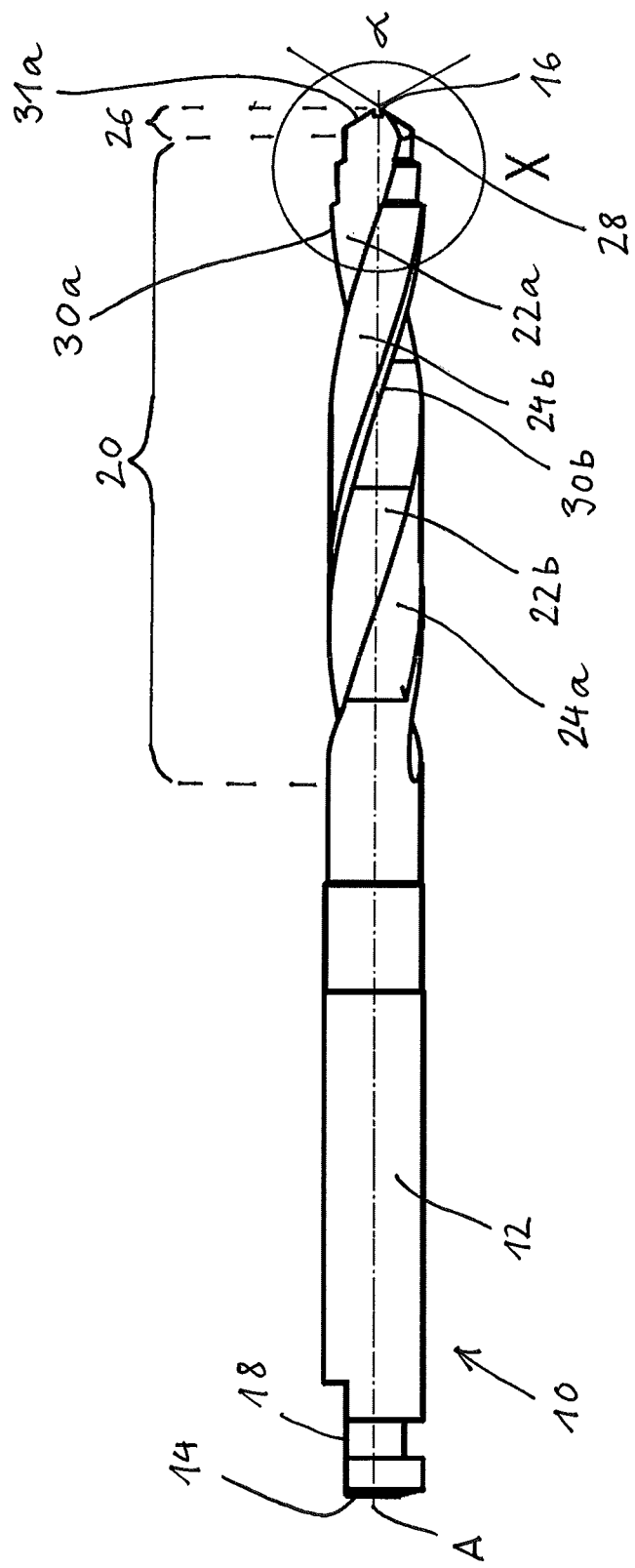
FIG. 4 shows a side view of a second embodiment of a dental drill according to the first concept of the present invention from a direction of view perpendicular to the central axis.
Figure 5:
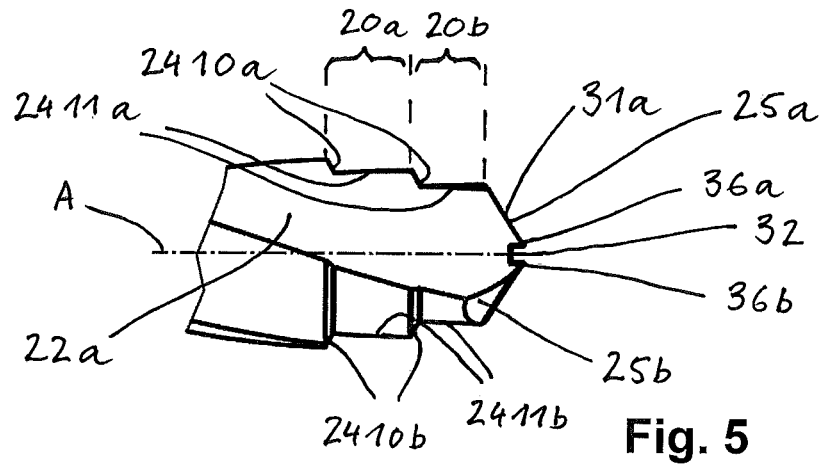
FIG. 5 shows a magnified view of the distal end region the embodiment shown in FIG. 4 marked as detail X in FIG. 4.
Figure 6:
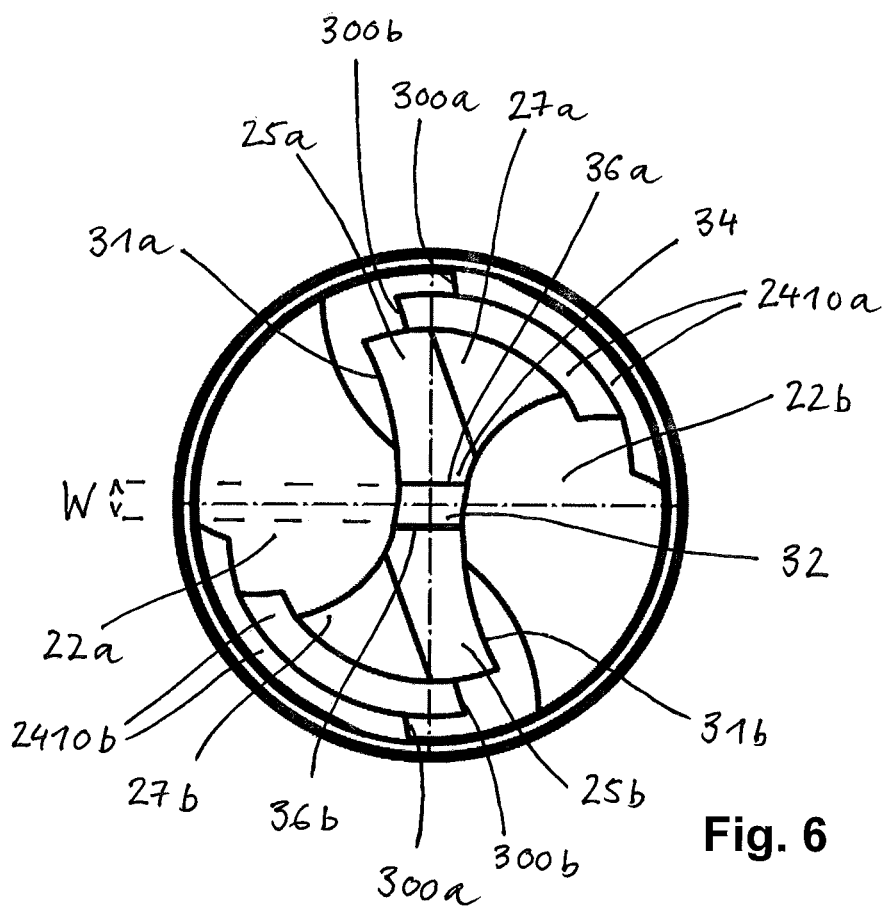
FIG. 6 shows a front view of the drill tip of the embodiment shown in FIG. 4 from a direction of view along the central axis.
Figure 7:
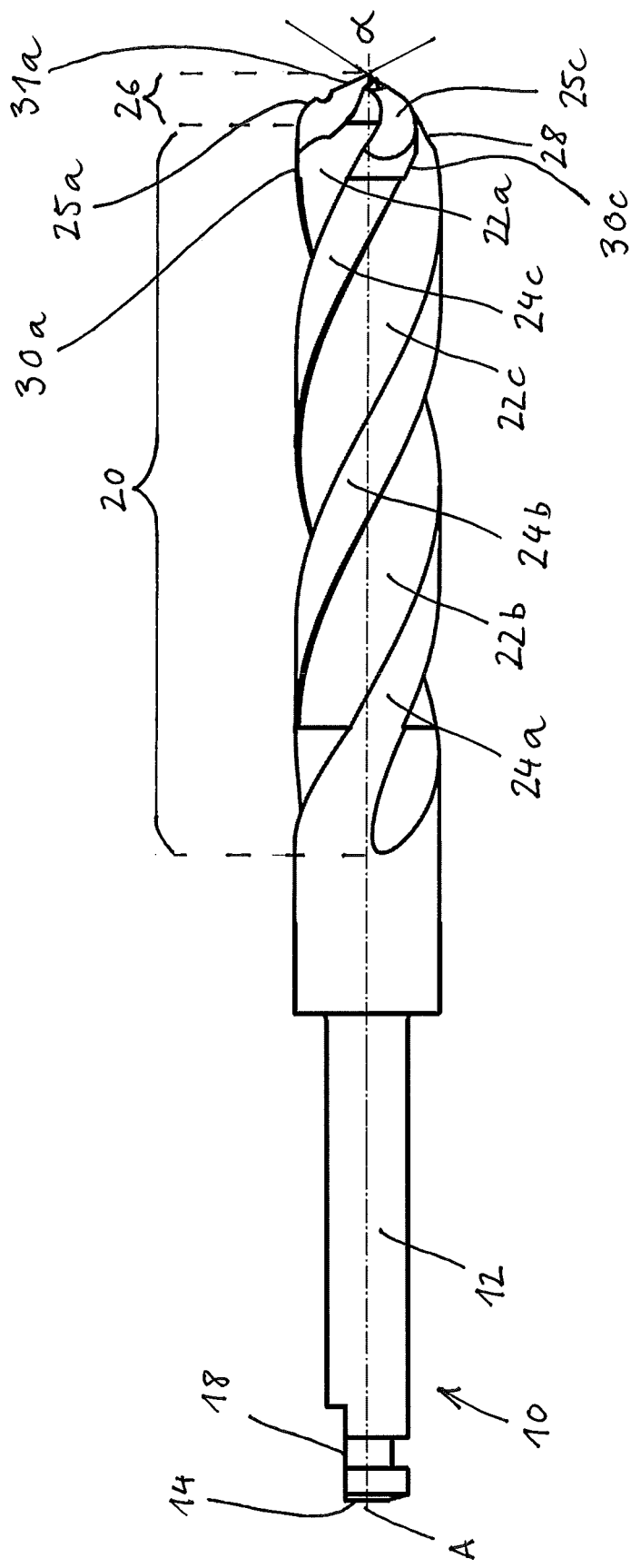
FIG. 7 shows a side view of a first embodiment of a dental drill according to the second concept of the present invention from a direction of view perpendicular to the central axis.

All embodiments of the figures relate to a dental drill 10 extending along the central axis A from a proximal end 14 to a distal end 16. The drill 10 is made from TAN, although other titanium alloys, such as TAV, could alternatively be used.

The dental drill comprises a shank 12 which is designed to cooperate with a drive tool, e.g. a dental handpiece, and to this end has an anti-rotation portion 18 arranged in a proximal end region of the drill adapted to receive torque from the drive tool.

The dental drill further comprises a flute portion 20 arranged distally to and running coaxially with the shank 12.

In the embodiments shown in FIGS. 1 to 3 and 4 to 6, respectively, which relate to preferred designs of drills of relatively small cutting diameter, the flute portion 20 comprises two flutes 22a, 22b extending along the flute portion 20, said flutes being interposed by lands 24a, 24b. Both the flutes 22a, 22b and the lands 24a, 24b run helically along the flute portion 20. In the specific embodiments shown, the width of the lands 24a, 24b is not constant over the length of the flute portion 20, but decreases in the distal direction towards the drill point 26; this decrease in the land width goes along with an increase in the depth of the flutes 22a, 22b and a reduction in the diameter of the web. Thus, in these embodiments, the diameter of the web is reduced in the distal direction while the overall diameter of the flute portion remains constant.

Directly adjoining the flute portion 20 at its distal end 28, a drill point 26 is formed comprising flanks 25a, 25b which taper radially inwardly in a distal direction toward the central axis A of the dental drill 10, the tapering being defined by a point angle α, which in the embodiments shown in FIGS. 1 to 3 and FIGS. 4 to 6 is about 120°. Each of the two lands 24a, 24b comprise a cutting edge 30a, 30b, which is formed at the intersection of the flute 22a, 22b with the leading edge of the land 24a, 24b following the respective flute in the direction of rotation of the drill. Thus, cutting edge 30a is formed at the intersection of flute 22a with the leading edge of land 24a and cutting edge 30b is formed at the intersection of flute 22b with the leading edge of land 24b. In the embodiments shown, the cutting edges 30a, 30b are helical. Alternatively, the flutes and cutting edges can also be straight.

In the drill point 26, two cutting edges 31a, 31b are formed by the leading edges of flanks 25a, 25b. These primary cutting edges 31a, 31b provide axial cutting action, whereas in the flute portion 20, the cutting edges 30a, 30b provide radial cutting action.

In the embodiments according to the first concept shown in FIGS. 1 to 3 and FIGS. 4 to 6, a central groove 32 is formed in web 34 at the distal end of the drill point 26, said groove 32 running perpendicular to the central axis A between the bases of the flutes 22a, 22b. Thus, two non-central ridges 36a, 36b are formed, which are arranged on either side of the groove 32 and distanced by the groove width W. These two non-central ridges 36a, 36b form the distal most ends of the flanks 25a, 25b, and are radially remote from the central axis A.

With regards to the dimensions of the embodiments shown in FIGS. 1 to 3 and 4 to 6, the cutting diameter (defined by the outer circumference of the flute portion 20) is in both cases about 2.2 mm, although the same design could also be used at larger diameters.

In both embodiments, the relief angle of the flanks 25a, 25b is 15°. The trailing surface 27a, 27b of each flank 25a, 25b is angled by a greater amount, approximately 40°, in order to increase the bite of the drill 10 without making this too aggressive and the central groove 32 has a groove width of 0.2 mm and a groove depth of 0.2 mm.

The feature of the present invention of having at least one of the flanks not extending to the central axis is realized differently in the embodiments shown in FIGS. 7 to 9 and FIGS. 10 to 13, respectively, relating to the second concept described above.

According to the embodiments shown in FIGS. 7 to 9 and 10 to 13, the flute portion 20 comprises three flutes 22a, 22b, 22c extending along the flute portion 20 and, hence, three lands 24a, 24b, 24c interposing the flutes 22a, 22b, 22c. Also in these specific embodiments, both the flutes 22a, 22b, 22c and the lands 24a, 24b, 24c run helically along the flute portion 20.

In analogy to the description of the embodiments of the first concept, drill point 26 comprises flanks 25a, 25b, 25c which taper radially inwardly in the distal direction toward the central axis A, the tapering being defined by a point angle α, which in the embodiment shown in FIGS. 7 to 9 and FIGS. 10 to 13 is about 132°.

Each of the lands 24a, 24b, 24c comprise a cutting edge 30a, 30b, 30c; specifically, cutting edge 30a is formed at the intersection of flute 22a with the leading edge of land 24a, cutting edge 30b is formed at the intersection of flute 22b with the leading edge of land 24b and cutting edge 30c is formed at the intersection of flute 22c with the leading edge of land 24c. However, these cutting edges 30a, 30b, 30c are blunted along the majority of the flute portion 20 in order to limit side cutting. Consequently, cutting edges 30a, 30b, 30c are only present at in the distal end region of the flute portion 20.

In the drill point 26, three cutting edges 31a, 31b, 31c are formed by the leading edges of flanks 25a, 25b, 25c. These primary cutting edges 31a, 31b, 31c provide axial cutting action. In contrast to the embodiments of FIGS. 1 to 3 and 4 to 6, cutting edges 31a, 31b, 31c are straight and formed in part by web thinning grooves 33a, 33b, 33c. These grooves 33a, 33b, 33c cut into the web 34 of the drill point 26 and lengthen the cutting edges 31a, 31b, 31c. In addition, two of these grooves 33a, 33c extend across the radially innermost part of the neighbouring flank 25c, 25b, thus effectively "cutting off" these flanks 25c, 25b. As a result the distal most end 37b, 37c of these flanks 25b, 25c are radially remote from the central axis A, reducing the material at the central axis A. In contrast, groove 33b terminates short of flank 25a, and hence the distal most end 37a of this flank, and cutting edge 31a, is located at the central axis A.

As mentioned above, this second concept is particularly suitable for dental drills having three flutes, and thus also having a larger cutting diameter, which is reflected by the embodiments shown in FIGS. 7 to 9 and 10 to 13 having a cutting diameter (corresponding to the outer circumference of the flute portion 20) of 4.2 mm, although a similar geometry could also be used in both larger (e.g. up to 7 mm) and smaller (e.g. down to 2.5 mm) cutting diameter drills. In both embodiments according to FIGS. 7 to 9 and 10 to 13, the relief angle of flanks 25a, 25b, 25c is 25°. This is more aggressive than the relief angles commonly found in stainless steel drills and enables the softer titanium or titanium alloy drills to effectively cut through bone.

Figure 8:
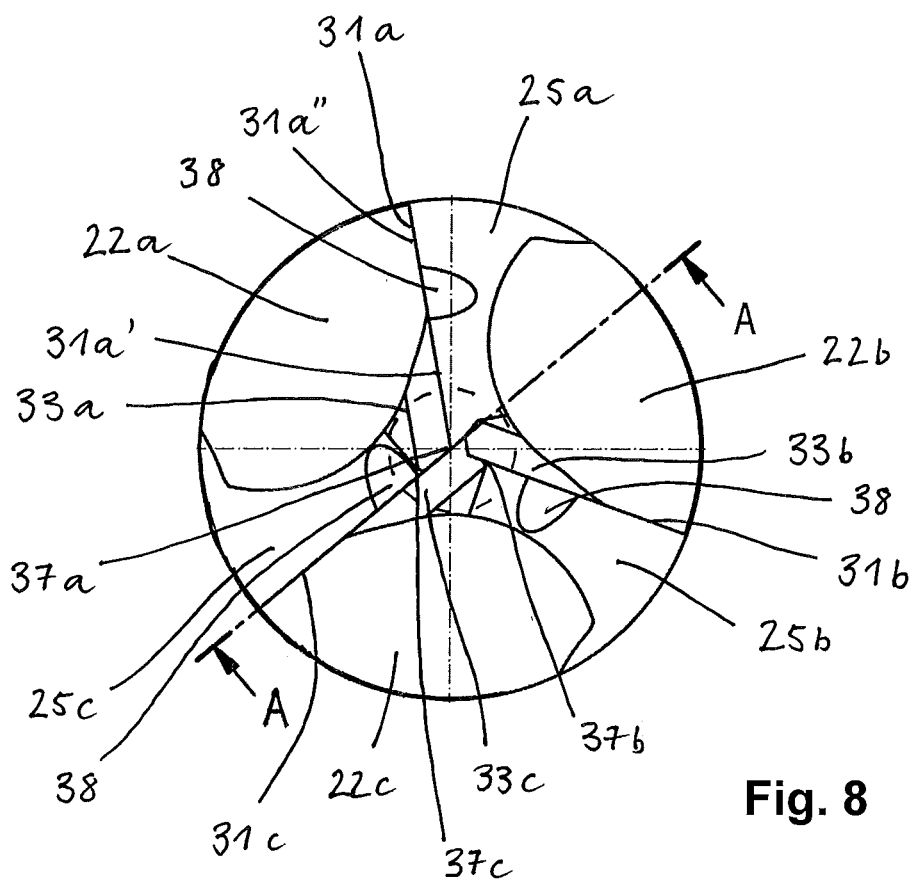
FIG. 8 shows a front view of the drill tip of the embodiment shown in FIG. 7 from a direction of view along the central axis.
Figure 9:
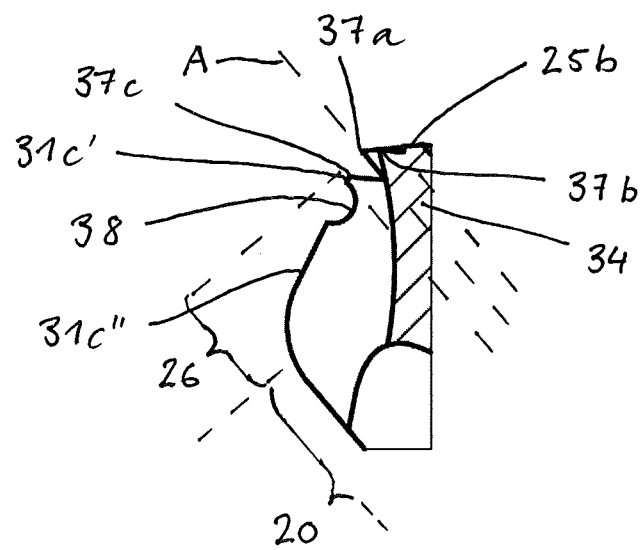
FIG. 9 shows a portion of the drill tip shown in FIG. 8 in a cross-section along plane A-A defined in FIG. 8.
Figure 10:
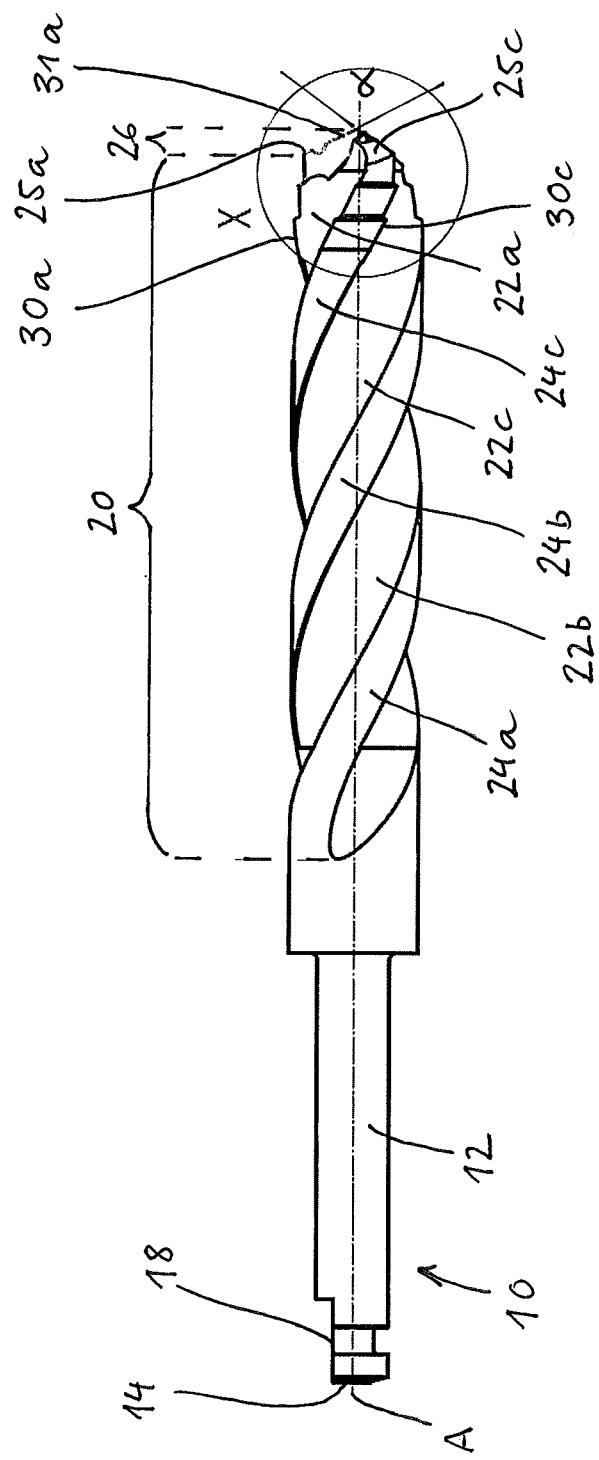
FIG. 10 shows a side view of a second embodiment of a dental drill according to the second concept of the present invention from a direction of view perpendicular to the central axis.
Figure 11:
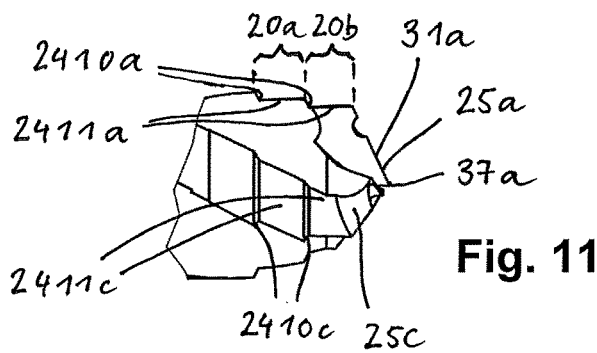
FIG. 11 shows a magnified view of the distal end region of the embodiment shown in FIG. 10 marked as detail X in FIG. 10.
Figure 12:
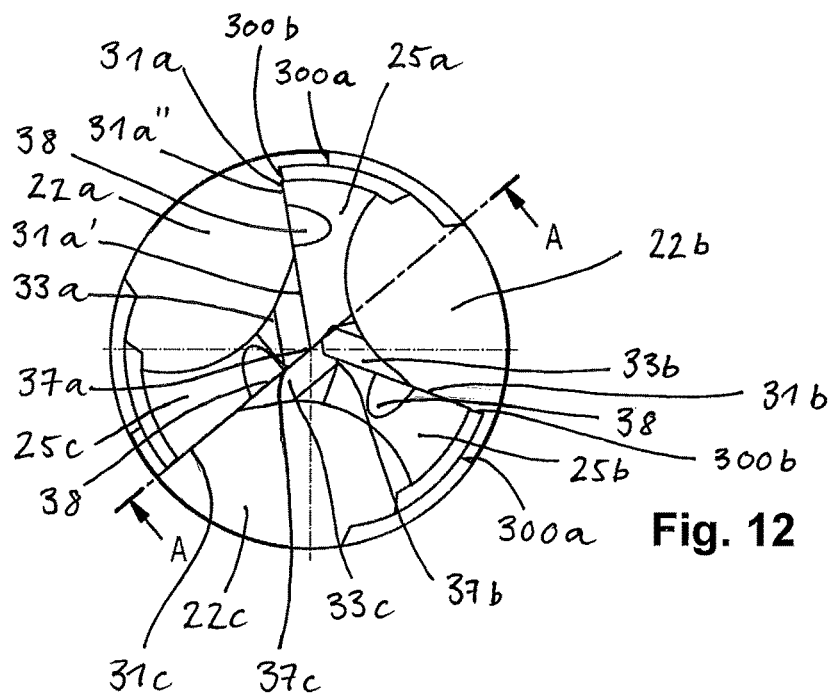
FIG. 12 shows a front view of the drill tip of the embodiment shown in FIG. 10 from a direction of view along the central axis.
Figure 13:
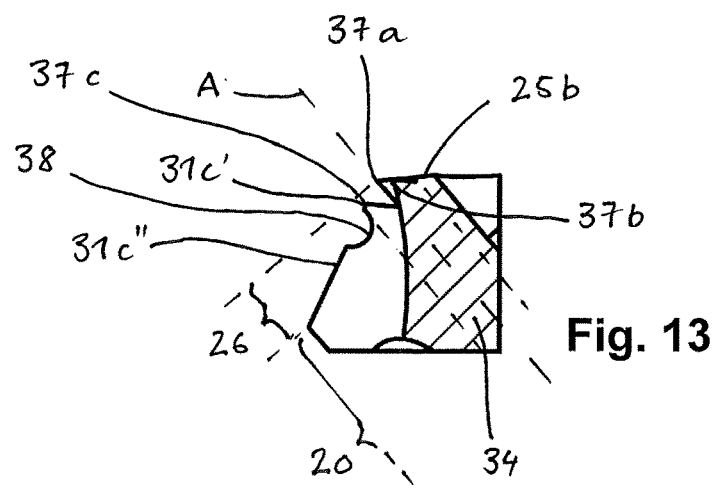
FIG. 13 shows a portion of the drill tip shown in FIGS. 11 and 12 in a cross-section along plane A-A defined in FIG. 11.

In addition, the embodiments according to FIGS. 7 to 9 and 10 to 13 further comprise the preferred feature that the cutting edges 31a, 31b, 31c are each interrupted by a groove 38, rendering the cutting edges discontinuous. By means of the interrupting groove 38, each cutting edge is divided into a pair of cutting edge portions, both cutting edge portions of the same pair running in the same plane and extending on either side of the interrupting groove 38. Specifically, cutting edge portions 31a', 31a" are shown in FIG. 8 and FIG. 12 for cutting edge 31a and cutting edge portions 31c', 31c" are shown in FIG. 9 and FIG. 13 for cutting edge 31c.

As further shown in FIGS. 8 and 12, the interrupting groove 38 is for each cutting edge 31a, 31b, 31c arranged at a different radial distance from the central axis A. Thus, the interrupting grooves 38 of the different cutting edges 31a, 31b, 31c are staggered relative to each other.

Although an interrupting groove 38 is only shown for the embodiments according to FIGS. 7 to 9 and 10 to 13, an interrupting groove can likewise be provided in the embodiments shown in FIGS. 1 to 3 and 4 to 6, thus rendering at least one of the two cutting edges of these embodiments discontinuous.

In distinction to the embodiments shown in FIGS. 1 to 3 and 7 to 9, the flute portions 20 of the embodiments shown in FIGS. 4 to 6 and FIGS. 10 to 13 comprise two stepped portions 20a, 20b, the diameter of which decreases in the distal direction in a step-wise manner. This is realized by the lands 24a, 24b (and 24c in the embodiment of FIGS. 10 to 13) tapering inwardly in a step-wise manner. Thus, for each land, a series of radially inwardly tapered steps 2410a, 2410b (and 2410c in the embodiment of FIGS. 10 to 13) is formed, which are interposed by portions 2411a, 2411b (and 2411c in the embodiment of FIGS. 10 to 13). In the present embodiments these portions 2411a, 2411b, 2411c are back tapered, i.e. they taper inwards slightly in the proximal direction, however in other embodiments these portions may be cylindrical. Apart from the primary cutting edges 31a, 31b (and 31c in the embodiment of FIGS. 10 to 13) of the drill point 26, additional axial cutting edges 300 are thereby formed by the steps 2410a, 2410b, 2410c. A first set 300a of these cutting edges 300 taper inwardly from the maximum circumference of the flute portion 20 to a first reduced diameter and the second set 300b taper inwardly from the first reduced diameter to a second reduced diameter. According to these specific embodiments, the cutting edges 300 on each step are staggered, as in particular shown in FIG. 6 and FIG. 12.

The above described embodiments are for illustrative purposes only and the skilled person will realize that alternative arrangements are possible which fall within the scope of the claims. For example, a drill can be provided having three flanks, all of which are cut off by grooves such that the distal most ends of the flanks are located radially remote from the central axis. Furthermore the drill points shown in FIGS. 1 to 3 and 4 to 6 could also be used in drill with larger cutting diameters and/or with interrupting grooves. Additionally the drills shown in FIGS. 6 to 9 and 10 to 13 may be produced without the interrupting grooves or with additional numbers of such grooves.

LIST OF REFERENCE NUMERALS 10 dental drill
12 shank
14 proximal end
16 distal end
18 anti-rotational portion
20 (20a,b) flute portion (stepped portions)
22 flute
24 land
25 flank
2410 tapered step of land
2411 portion interposing tapered steps
26 drill tip
27 trailing surface of flank
28 distal end of the flute portion
30 cutting edge of land
300 primary cutting edge of step
31 (primary) cutting edge of flank
32 groove
33 web thinning groove
34 web
36 non-central ridge
37 distal most end of flank
38 cutting edge-interrupting groove
A central axis
W groove width

The invention claimed is:

1. A dental drill configured for forming a hole in an oral cavity, formed of titanium or a titanium alloy having a hardness greater than pure titanium, said drill extending along a central axis from a proximal end to a distal end, the drill comprising a shank arranged in a proximal end region of the drill and extending along the central axis, a flute portion arranged distally to and running coaxially with the shank said flute portion comprising two or more flutes extending along the flute portion and being interposed by lands, the flute portion further comprising a central solid web and a drill point directly adjoining the distal end of the flute portion and comprising two or more flanks which taper radially inwardly from the distal end of each land in the distal direction toward the central axis, each flank comprising a cutting edge, wherein at the distal end of the drill point at least one groove is formed in the web such that the distal most end of at least one of the flanks is located radially remote from the central axis.

2. The dental drill as claimed in claim 1, wherein said at least one groove is provided such that the distal most end of all of the flanks are located radially remote from the central axis.

3. The dental drill as claimed in claim 2, wherein an equal number of grooves and flanks is provided, one groove being located across the radially innermost portion of each flank such that the distal most end of each flank is radially remote from the central axis.

4. The dental drill as claimed in claim 2, wherein the flute portion comprises exactly two flutes interposed by exactly two lands and the drill point comprises exactly two flanks, a central groove being formed at the distal end of the drill point, said groove running through the central axis across the web of the drill such that the distal most ends of both flanks are located radially remote from the central axis.

5. The dental drill as claimed in claim 4, having a cutting diameter of 2.5 mm or less.

6. The dental drill as claimed in claim 4, wherein the cutting edges are curved.

7. The dental drill as claimed in claim 1, wherein the distal most end of at least one flank is located at the central axis and the at least one groove is formed in the web such that the distal most end of at least one flank is located radially remote from the central axis.

8. The dental drill as claimed in claim 7, wherein the cutting edge of said at least one flank whose distal most end is located at the central axis is positioned on the flank such that said cutting edge extends to the central axis.

9. The dental drill as claimed in claim 7, wherein the distal most end of a single flank is located at the central axis and at least one groove is formed in the web such that the distal most end of the one or more remaining flank is located radially remote from the central axis.

10. The dental drill as claimed in claim 7, wherein said at least one groove is arranged to extend the cutting edge of one flank radially inwards into the web while also cutting across the radially innermost part of a neighbouring flank, such that the distal most end of the neighbouring flank is radially remote from the central axis, the drill point further comprising at least one additional web thinning groove which is arranged to extend the cutting edge of one flank radially inwards into the web but which does not cut across the radially innermost part of a neighbouring flank, such that the distal most end of this flank is located at the central axis.

11. The dental drill as claimed in claim 7, wherein the cutting edges of the two or more flanks are straight.

12. The dental drill as claimed in claim 1 wherein the flute portion comprises at least three flutes interposed by at least three lands and the drill point comprises at least three flanks.

13. The dental drill as claimed in claim 1, wherein the flute portion comprises exactly three flutes and exactly three lands and the drill point comprises exactly three flanks.

14. The dental drill as claimed in claim 1, having a cutting diameter of at least 2.5 mm.

15. The dental drill as claimed in claim 1, wherein each flank has a relief angle of at least 18°.

16. The dental drill as claimed in claim 1, wherein the drill is formed of a titanium alloy having a greater hardness than pure titanium.

17. The dental drill as claimed in claim 16, wherein the drill is formed of a titanium-aluminium-niobium alloy or a titanium-aluminium-vanadium alloy.

18. The dental drill as claimed in claim 1, wherein at least one of the cutting edges is interrupted by at least one groove to form a discontinuous cutting edge.

19. The dental drill as claimed in claim 18, wherein the at least one interrupting groove is located at a different radial location in each cutting edge, such that the grooves of the different cutting edges are staggered relative to each other.

20. The dental drill as claimed in claim 1, wherein the flute portion comprises one or more stepped portion.

21. The dental drill as claimed in claim 1, wherein the drill is matted.

* * * * *